(12) United States Patent
Salazar (10) Patent No.: US 7,834,064 B2
(45) Date of Patent: Nov. 16, 2010

(54) CLINICAL METHOD FOR THE IMMUNOMODULATORY AND VACCINE ADJUVANT USE OF POLY-ICLC AND OTHER DSRNAS

(76) Inventor: Andres Mario Salazar, 3203 Cleveland Ave., NW., Washington, DC (US) 20008

( * ) Notice: Subject to any disclaimer, the term of this patent is extended or adjusted under 35 U.S.C. 154(b) by 296 days.

(21) Appl. No.: 11/291,851

(22) Filed: Dec. 2, 2005

(65) Prior Publication Data

US 2006/0223742 A1    Oct. 5, 2006

Related U.S. Application Data

(60) Provisional application No. 60/640,984, filed on Jan. 3, 2005.

(51) Int. Cl.
- *A61K 45/02* (2006.01)
- *A61K 37/02* (2006.01)
- *C07H 21/00* (2006.01)
- *C07C 103/52* (2006.01)

(52) U.S. Cl. .................. 514/889; 514/2; 514/44 R; 536/24.1; 536/25.2

(58) Field of Classification Search ............... None
See application file for complete search history.

(56) References Cited

U.S. PATENT DOCUMENTS

| 4,349,538 | A  * | 9/1982 | Levy .................. 514/44 |
| 6,468,558 | B2 * | 10/2002 | Wong ................ 424/450 |
| 2004/0101513 | A1 * | 5/2004 | Zuckermann ......... 424/93.2 |
| 2006/0205693 | A1 * | 9/2006 | Stein et al. ............ 514/81 |

OTHER PUBLICATIONS

Salazar et al. Neurosurgery 1996, vol. 38, pp. 1096-1104.*
Chang et al., Expert Rev. Vaccines 2004, vol. 3, pp. 199-220.*
Old, Cancer Immunity 2008, vol. 8 Suppl. 1, pp. 1-4.*
Singh, Virology Journal 2006, vol. 3, pp. 60-67.*
Sasaki et al. Journal of Virology 1998, vol. 72, pp. 4931-4939.*
Locher et al. DNA and Cell Biology 2004, vol. 23, pp. 107-110.*

* cited by examiner

*Primary Examiner*—Sean R McGarry
(74) *Attorney, Agent, or Firm*—Herman Hohauser (57) ABSTRACT

An improved understanding and method for the clinical adjuvant and immunomodulatory use of dsRNAs and ply-ICLC in particular, alone or in conjunction with other drugs and various vaccines designed to prevent or treat various microbial, viral, neoplastic, autoimmune diseases, and or degenerative diseases.

1 Claim, 5 Drawing Sheets

Figure 1. Systemic Response to a Single Intranasal dose of Poly-ICLC in Rhesus Monkeys

| Monkey # | Plasma Interferon titer Baseline (Intl. U) | Plasma Interferon titer 24 Hours (Intl. U) |
|---|---|---|
| CE 5 F | <3 | 200 |
| CF 61 | <3 | 200 |
| CF 67 | <3 | 700 |
| CF4J | <3 | 700 |
| CF 8F | <3 | 700 |
| CF 5X | <3 | <3 |
| CF 45 | <3 | 100 |
| CF 4R | <3 | 200 |

Figure 2.

Figure 3. P56 Response to IM Poly-ICLC in Humans

Figure 4 IM Poly-ICLC in Smallpox Vaccination of Patas Monkeys

Vaccination plus poly-ICLC on day 0. Viral rechallenge alone on day 28.

Figure 5: Percent Survival of Malignant Glioma Patients treated with Poly-ICLC 20 mcg/kg IM two to three times weekly for 1 to 4 years.

| Survival | GBM<br>12 patients | AA<br>11 patients | AA (pf)<br>11 patients |
|---|---|---|---|
| 1 yr | 92% (50%†) | 100% | 100% |
| 2 yr | 50% | 100% (50%†) | 91% |
| 3 yr | 25% (2.2%†) | 91% | 82% |
| 4 yr | 17% | 91% | 82% |
| 5 yr | 8% | 91% | 73% |
| 8 yr | 8% | 82% | 36% |

GBM = glioblastoma, AA = anaplastic astrocytoma, pf = progression free survival, † = Expected survival on standard treatment with radiation and chemotherapy.

Figure 6. Poly-ICLC Treatment of AIDS, Viral Load
Group I: Poly-ICLC Plus Zidovudine

| PATIENT Number | P-24 Antigenemia (pcg/ml) | | | | | | |
|---|---|---|---|---|---|---|---|
| | Months Base | 4 | 8 | 12 | 16 | 20 | 24 |
| PR-O1 | 89 | 15 | 21 | 305 | D | D | D |
| PR-O2 | 45 | 20 | 140 | - | D | D | D |
| PR-O3 | 0 | 80 | 34 | - | D | D | D |
| PR-O4 | 0 | - | 78 | 0 | 0 | 0 | 0 |
| PR-05 | 0 | - | - | - | - | - | - |
| PR-06 | 200 | - | 310 | D | D | D | D |
| PR-O7 | - | 346 | 35 | - | D | D | D |
| PR-O8 | - | 78 | 42 | 0 | 0 | 0 | 0 |
| 04-056 | 12 | 0 | 57 | - | D | D | D |
| PR-10 | 72 | - | - | 0 | 0 | 0 | - |
| PR-11 | 80 | 37 | - | 0 | 0 | 0 | - |
| PR-12 | 76 | 37 | - | 0 | 0 | 0 | - |
| PR-13 | 85 | - | 16 | 11 | 0 | D | D |
| PR-16 | 0 | 0 | 0 | 0 | - | - | - |
| PR-24 | 0 | 0 | 0 | 0 | - | - | - |

Group II: Poly-ICLC Alone

| PATIENT Number | P-24 Antigenemia (pcg/ml) | | | | |
|---|---|---|---|---|---|
| | Base | 4 | 8 | 12 | 16 |
| PR-15 | 0 | 0 | 0 | D | D |
| PR-17 | 0 | 0 | 0 | 0 | - |
| PR-18 | 0 | - | 0 | 0 | - |
| PR-19 | 117 | 31 | D | D | D |
| PR-20 | 0 | 0 | 0 | 0 | - |
| PR-21 | 0 | 0 | 0 | 0 | - |
| PR-22 | 0 | 0 | 0 | 0 | - |
| PR-23 | 808 | 704 | 440 | 200 | - |

(-) = Not done, (D) = Died

Figure 7. Poly-ICLC Treatment of Progressive Multiple Sclerosis

CHRONIC-PROGRESSIVE MS

| SEX/AGE | Mos. On PICLC | EDSS-E | AI-E | EDSS-L | AI-L | EDSS Change | Change Per yr. |
|---|---|---|---|---|---|---|---|
| F/29 | 128 | 7 | 8 | 8.5 | 9 | 1.5 | 0.1 |
| F/35 | 82 | 8.5 | 9 | 10 | 9 | 1.5 | 0.2 |
| M/25 | 27 | 7 | 8 | 10 | 9 | 3 | 1.3 |
| M/42 | 189 | 5 | 5 | 7.5 | 6 | 2.5 | 0.2 |
| F/39 | 136 | 8 | 9 | 9 | 9 | 1 | 0.1 |
| M/28 | 12 | 6 | 5 | 5.5 | 3 | -0.5 | -0.5 |
| M/22 | 45 | 7.5 | 7 | 8.5 | 9 | 1 | 0.3 |
| F/61 | 121 | 6.5 | 5 | 8 | 5 | 1.5 | 0.1 |
| M/49 | 164 | 6 | 4 | 6.5 | 6 | 0.5 | 0.0 |
| F/39 | 114 | 8 | 8 | 8 | 8 | 0 | 0.0 |
| M/46 | 13 | 9 | 9 | 7 | 7 | -2 | -1.8 |
| M/25 | 42 | 7 | 6 | 7.5 | 8 | 0.5 | 0.1 |
| F/59 | 26 | 5.5 | 4 | 6 | 3 | 0.5 | 0.2 |
| M/41 | 25 | 8.5 | 9 | 8.5 | 9 | 0 | 0.0 |
| F/62 | 6 | 7.5 | 8 | 7.5 | 8 | 0 | 0.0 |
| M/23 | 10 | 5.5 | 3 | 4.5 | 3 | -1 | -1.2 |
| F/50 | 85 | 6.5 | 6 | 7 | 6 | 0.5 | 0.1 |
| F/41 | 60 | 6.5 | 6 | 9 | 9 | 2.5 | 0.5 |
| F/35 | 126 | 8 | 8 | 8 | 9 | 0 | 0.0 |
| MEDIAN | 60 | 7.0 | 7.0 | 8.0 | 8.0 | 0.5 | 0.09 |

EXACERBATING PROGRESSIVE MS

| SEX/AGE | Mos. On PICLC | EDSS-E | AI-E | EDSS-L | AI-L | EDSS Change | Change Per yr. |
|---|---|---|---|---|---|---|---|
| F/36 | 4 | 9 | 9 | 3 | 2 | -6 | -18.0 |
| F/34 | 35 | 5.5 | 2 | 6 | 3 | 0.5 | 0.2 |
| F/26 | 68 | 4.5 | 0 | 5 | 2 | 0.5 | 0.1 |
| F/55 | 85 | 4 | 2 | 3.5 | 2 | -0.5 | -0.1 |
| F/35 | 84 | 3 | 2 | 3.5 | 3 | 0.5 | 0.1 |
| M/42 | 28 | 6 | 4 | 6 | 4 | 0 | 0.0 |
| F/25 | 63 | 9.5 | 9 | 4 | 2 | -5.5 | -1.0 |
| M/22 | 3 | 8.5 | 9 | 6 | 6 | -2.5 | -10.0 |
| F/14 | 57 | 8.5 | 9 | 4.5 | 2 | -4 | -0.8 |
| F/54 | 9 | 8.5 | 9 | 8.5 | 8 | 0 | 0.0 |
| F/29 | 12 | 5 | 3 | 1 | 1 | -4 | -4.0 |
| F/34 | 25 | 5.5 | 3 | 5.5 | 3 | 0 | 0.0 |
| F/17 | 83 | 9.5 | 9 | 3 | 2 | -6.5 | -0.9 |
| MEDIAN | 35 | 6.0 | 4.0 | 4.5 | 2.0 | -0.5 | -0.1 |

EDSS-E = Kurtzke Disability Status Score on Entry; EDSS-L = EDSS at Last examination; EDSS range from 1 (mild MS) to 9 (totally disabled)
AI-E = Ambulation Index on study entry; AI-L = AI at Last Examination
AI ranges from 1 (minimal disability) to 9 (bedridden)

CLINICAL METHOD FOR THE IMMUNOMODULATORY AND VACCINE ADJUVANT USE OF POLY-ICLC AND OTHER DSRNAS

CROSS REFERENCE TO RELATED APPLICATION

This application is a Conversion of Provisional Application 60/640,984 filed on Jan. 3, 2005

FIELD AND BACKGROUND OF THE INVENTION

1. Field of the Invention

The present invention relates in general to methods for clinical administration of pharmaceutical compounds, and more particularly to double-stranded ribonucleic acids (dsRNAs), and more particularly to polyriboinosinic-polyribocytidylic acid stabilized with polylysine and carboxymethylcellulose (Poly-ICLC).

2. Background Information

The invention described and claimed herein comprises an improved method for the adjuvant and immunomodulatory use of dsRNAs and poly-ICLC in particular, alone or in conjunction with other drugs and various vaccines designed to prevent or treat various microbial, viral, neoplastic, autoimmune diseases and or degenerative diseases. DsRNAs are not normally found in mammalian cells, but are components of many viruses or byproducts of viral replication. As a result, they are identified as "foreign" or as pathogen associated molecular patterns (PAMPs) by mammalian host defense systems and are potent activators of the immediate innate immune response as well as of longer-term adaptive immunity, in some ways serving as a bridge between the two systems. Poly-ICLC, a stabilized synthetic dsRNA viral mimic, has been among the more therapeutically promising, clinically available of these, and has been demonstrated to have broad antiviral, antiproliferative, immune modulating and gene regulatory actions. While some of these actions have been known for several years, their translation to practical therapeutic application has remained elusive, and after over two decades, dsRNAs, and poly-ICLC in particular, have yet to be approved by the US Food and Drug Administration (FDA) for any clinical indication.

The reasons for this failure of clinical translation are multiple, and may include dosage, administration schedule or timing, toxicity, host species, and the particular dsRNA formulations tested. The dose, dosage schedule, structure and size of dsRNA species can have a critical impact on the shape of their biological activity, as well as an impact on the cost, precision and reproducibility of manufacture, which can in turn be critical considerations in the regulatory and commercialization process. For example, it was discovered some years ago that a potent nuclease found in the serum of primates, poultry and certain other species will degrade plain dsRNA and render it inactive as an interferon inducer or antiviral agent. One solution to this problem was to stabilize poly-IC with poly-lysine, resulting in the compound poly-ICLC, which is highly active in humans and other primates. Other approaches are liposomal encapsulation of poly-ICLC or the use of mismatched poly-IC. Different dsRNA species will also have differential biological effects. Likewise, particular host or pathogen/neoplasm-associated factors can profoundly affect the response to various PAMPs, including dsRNAs. As a simple, stable, synthetic, non-replicating dsRNA with no specific genetic message, poly-ICLC in some ways represents an ideal viral mimic or PAMP. As such, while it non-specifically activates a panoply of host defenses, it also lacks the ability to inhibit any of them. Some of these are discussed below.

To the extent that it may aid in the understanding of the method, U.S. Pat. No. 4,349,538 (Hilton B Levy) and U.S. Pat. No. 6,468,558 (Jonathan P Wong) and US Patent application 20040005998 (Andres Salazar) are incorporated herein by reference. Levy describes the preparation and some uses of poly-ICLC. However, the high doses (200-300 mcg/kg IV) described clinically by Levy were intended to induce interferon (IFN) and proved to be toxic and largely ineffectual for treatment of human patients, to the extent that, after many attempts, the experimental clinical use of high dose poly-ICLC was largely discontinued almost two decades ago. However, lower dose (10 to 50 mcg/kg) poly-ICLC is associated with little or no toxicity with an apparent enhancement of certain clinical activities. (Salazar, Levy et al. 1996))

U.S. Pat. No. 4,349,538 to Levy, in the summary of the invention, disclosed therein provides a nuclease-resistant hydrophilic complex of high molecular weight In.Cn with relatively low molecular weight poly-1-lysine and carboxymethylcellulose. The In.Cn of the complex has a molecular weight in the range of from about $7.\text{times}.10.\text{sup}.5$ daltons to about $1.\text{times}.10.\text{sup}.7$ daltons, and the poly-1-lysine of such complex has a molecular weight within the range from about 13,000 daltons to about 35,000 daltons with a range of about 17,000 daltons to about 28,000 daltons being preferred and a range of about 27,000 daltons to about 28,000 daltons being optimum. At molecular weights below about 13,000 daltons interferon is not produced. At molecular weights above about 35,000 daltons the complex produced is restrictively antigenic. In another embodiment, a poly-1-lysine range of 13,000 to 28,000 daltons may be used.

Non-toxic and non-antigenic injectable preparations of the complex of the present invention are preferably prepared by providing separate solutions of each of the three components of the complex in a pharmaceutically acceptable aqueous carrier such as pyrogen-free saline, and first mixing the poly-1-lysine solution with the carboxymethylcellulose solution, preferably by slowly pouring the former into the latter with stirring, and continuing the stirring to redissolve any precipitate thereby formed. For best results, such stirring is preferably continued for a period of time sufficient to achieve minimum turbidity in the solution, which generally requires 2 to 3 days. To the resulting solution of poly-1-lysine-carboxymethylcellulose complex, is then added the In.Cn solution, preferably followed by an additional 2 to 3 days of stirring, to form the final solution of In.Cn-poly-1-lysine-carboxymethylcellulose complex, abbreviated as poly(ICLC). The carboxymethylcellulose, which is a hydrophilic material negatively charged at a neutral pH is an essential part of the complex, since without its presence, the In.Cn and the poly-1-lysine would form an intractable precipitate. Moreover, the above-described order of addition of the components of the complex, i.e., first forming the poly-1-lysine-carboxymethylcellulose complex and thereafter adding the In.Cn thereto to form the final poly(ICLC) complex, is critical to the preparation of the complex since any other order of addition would result in the formation of an intractable precipitate.

While the biological actions of a viral mimic such as poly-ICLC are complex and closely interrelated, it may be useful to consider at least four groupings, any of which (alone or in combination) might be responsible for its antitumor and antiviral activity, as well as its adjuvant actions. These are 1) its induction of interferon and other cytokines; 2) its activation of specific enzymes, including oligoadenylate synthetase (OAS)

and the p68 protein kinase (PKR), 3) its multidimensional gene regulatory actions, and 4) its broader immune modulating effects.

Interferon Induction: Induction of interferon, various cytokines and chemokines is one of the important mechanisms for the action of poly-ICLC, but a full discussion of the actions of the interferons is beyond the scope of this submission. The functions of the interferons are still being elucidated, but interferon alone does not appear to be sufficient treatment for many conditions, including some that are responsive to poly-ICLC. Poly-ICLC is probably the most potent interferon inducer in man, with increasing doses of poly-ICLC resulting in higher serum interferon titers than are typically achievable by administration of exogenous interferon. However, as noted, such high IFN levels appear clinically counterproductive. In fact, in some cases the clinical therapeutic effects of low dose poly-ICLC do not appear to be associated with induction of measurable serum interferon levels, although interferon induction at the local level may still be playing an important biological role. Preliminary studies suggest that the induction of the "natural mix" of other cytokines and chemokines by poly-ICLC appears to track that of the interferons.

Unpublished pharmacokinetic studies in monkeys have shown that poly-ICLC itself drops off rapidly in serum after IV administration, as indicated by the interferon inducing ability of serum in tissue culture, which is down to 5% of peak at 4 hours. However, this is distinct from the biological effect itself in vivo, whereby serum interferon peaks at 4-24 hours, and OAS peaks at over two days. Repeated administration at daily intervals also reveals a "hyporesponsive" period after administration of poly-ICLC, with a transient drop in its interferon induction. As expanded below, these observations are important in the design of the most effective clinical or adjuvant dosing regimens for a PAMP such as poly-ICLC.

"Catalytic" Action of Poly-ICLC: OAS and PKR

The second action of poly-ICLC is a more direct antiviral and antineoplastic effect mediated by various interferon-inducible enzyme systems that trigger signaling cascades mediating the antiviral state. The 2'5' oligoadenylate synthetase (OAS) and the P1/eIF2a kinase, also known as the dsRNA dependent P68 protein kinase (PKR) are the best studied. (Jacobs and Langland 1996) Others described recently are the P56 protein and the RIG-I helicase system (Yoneyama, Kikuchi et al. 2004). Activation of the OAS and PKR by poly-ICLC appears to be at least a three-stage process: First, induction of interferon by poly-ICLC, then induction of the enzymes by the interferon, and finally, activation of the enzymes by the poly-ICLC. DsRNA thus functions as an obligatory cofactor for OAS, which activates ribonuclease-L, as well as for the PKR, which inhibits initiation of protein synthesis. This may help explain the demonstrated preferential decrease of tumor protein synthesis in vivo by poly-ICLC.

The OAS and PKR are very sensitive to dsRNA dose and structure. For example, simple, long chain dsRNA (as in poly-ICLC) is the most potent stimulator of OAS and PKR, while mismatched or irregular dsRNA can be inhibitory. Similarly, the PKR has both high and low affinity binding sites and is inhibited by too high a dose of dsRNA. (Galabru, Katze et al. 1989) Clinically, the OAS response is also maximal at a dose of about 30 mcg/kg poly-ICLC, and is much diminished above 100 mcg/kg (M. Kende, N. Bernton, et al., unpublished).

The clinical half-life of the OAS response to IM poly-ICLC is about 2.5 days, suggesting an optimum dose schedule of two or three times per week. Brain tumor patients so treated with poly-ICLC showed up to a 40-fold increase in serum OAS product in response to treatment at 10 to 50 mcg/kg, and a significant association of serum OAS with tumor response (p=0.03). (Salazar, Levy et al. 1996) Mediation of antitumor action by OAS and/or PKR activation could also help explain why the high doses of poly-ICLC used in early cancer trials were relatively ineffective.

Many viruses, including but not limited to adenovirus, pox viruses (vaccinia), Ebola virus, foot and mouth virus, influenza, hepatitis, poliovirus, herpes simplex, SV-40, reovirus, and the human immunodeficiency virus (HIV) circumvent host defenses by down regulating OAS and/or PKR, and in many cases, this effect can be reversed in vitro by exogenous dsRNA. (Jacobs and Langland 1996) A block of either PKR and/or OAS-mediated interferon action might also partly explain the variable response to interferons seen in both microbial and neoplastic disease. Certain viruses as well as neoplasms such as malignant gliomas may use this or a similar mechanism to circumvent host defenses and cause disease. Those diseases may thus be among the prime targets for clinical poly-ICLC therapy using the method described herein, which maximizes PKR activation.

The interaction of the type I interferons, other cytokines and poly-ICLC with each other in protection of the host from viral or neoplastic challenges remains unclear partly because of their overlapping functions and the multiple alternative signaling pathways involved. Nevertheless, the relationship of poly-ICLC and the interferons can be manipulated to therapeutic advantage. For example, at moderate to high doses, poly-ICLC is a powerful inducer of interferons, which in turn can modulate the immune system as well as induce synthesis of enzymes systems such as the OAS, PKR and others that themselves ultimately regulate specific protein synthesis. But, as noted above, the OAS, PKR, and likely others also require low-dose dsRNAs as obligatory cofactors to function, particularly if they have been blocked by viral and or neoplastic inhibition. Thus, double-dosing with poly-ICLC at approximately 24-48 hour intervals is postulated to be most effective.

Figure 4:
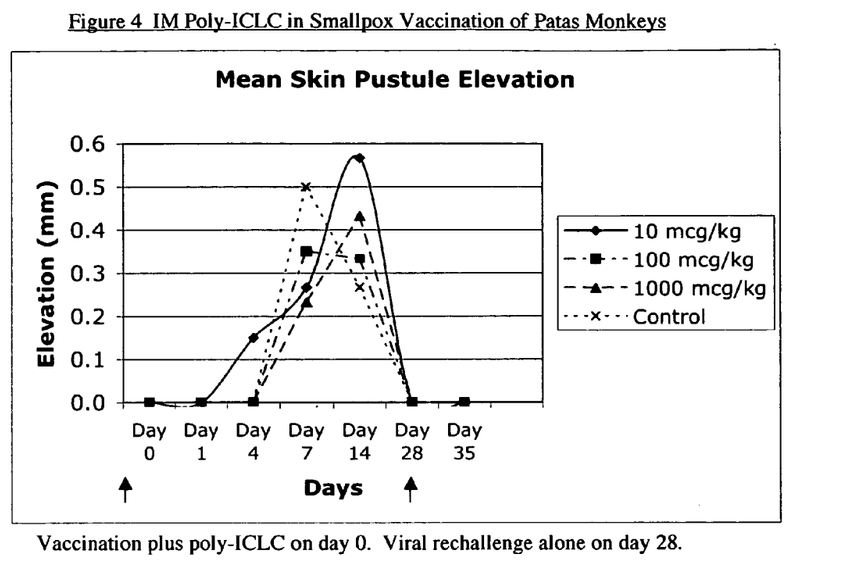
FIG. 4 is a drawing showing the interaction of poly-ICLC and DryVax vaccine during smallpox vaccination of Patas Monkeys. The lack of a skin lesion on rechallenge 28 days after primary vaccination with poly-ICLC and DryVax indicates that, despite its demonstrated antiviral action in murine and primate models of vaccinia, poly-ICLC in various doses does not interfere with the action of a live virus vaccine.

Clinical Implications: We have now shown that low dose poly-ICLC is particularly effective clinically when administered in this regimen. For example, malignant brain tumor patients receiving poly-ICLC alone every other day for prolonged periods of time (months to years) showed a reduction in their tumors and prolonged median survival (see FIG. 4) Similarly, working in avian cell culture, Marcus and colleagues showed marked enhancement of antiviral action by using the combination of exogenous interferon followed by poly-IC at 24 hours in that order (Marcus and Sekellick 2001). In this context, poly-ICLC may be serving at least two functions; the induction of interferon and other cytokines, and the later activation of the previously induced OAS, PKR, and other enzymes. Alternatively, this effect could also be mediated through induction of expression of TLR3 by Poly-ICLC and or interferon and its subsequent activation by repeated poly-ICLC dosing. In clinical or in-vivo situations, the activation of various elements of the immune system, including dendritic cells, NK cells and T lymphocytes also play an important role, discussed below.

Clinical Gene Regulation is a third mechanism by which poly-ICLC can modify the biologic response and provide therapeutic benefit.

Figure 3:
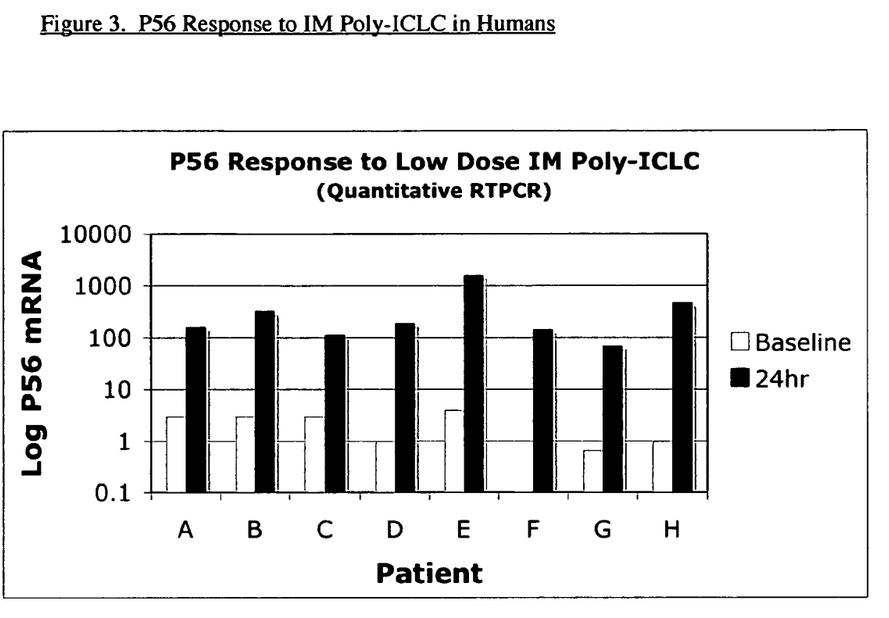
FIG. 3 is an unpublished table demonstrating marked clinical induction in humans of the antiproliferative and immune regulatory gene product P56. WBC of glioma patients receiving the regimen of poly-ICLC herein described IM showed enhanced expression of P56 on RT-PCR by 40 to 400 fold at 24 hours after the first dose.

Plain, unstabilized poly-IC has been shown to up-regulate or down-regulate a broad variety of over 270 genes in cell culture (Geiss, Jin et al. 2001). However plain poly-IC is not effective in vivo in primates and many other species, and is of limited clinical utility. Similarly, we have now demonstrated that poly-ICLC also has broad gene regulatory actions either in-vitro or when administered clinically to humans. (See FIG. 3) These genes include but are not limited to various viral restriction factors, glioma pathogenesis related factor, helicase, interferon induced protein (P56), tumor necrosis factor, glioma pathogenesis-related protein (GPRP), interferon regulatory factor, matrix metalloproteinase, plasminogen activator, tumor protein p53, fibroblast growth factor, eukaryotic initiation factor 2, actin filament-associated protein, and VCAM-1. Some of these genes play critical roles in the body's natural defenses against a variety of neoplasms and microbial infections, and in controlling other cell functions, including protein synthesis, atherogenesis, programmed (apoptotic) cell death, cell metabolism, cellular growth, the cytoskeleton and the extracellular matrix. The activation of viral restriction factors such as TRIM5a may be especially relevant to the potent role played by poly-ICLC in inducing the antiviral state. Gene activation appears to be transient, lasting 24-48 hours, suggesting that repeated dosing at 2-3 day intervals will be necessary to achieve a therapeutic effect in some conditions. This is the schedule of administration that we used successfully in treatment of malignant gliomas. (See FIG. 4 and (Salazar, Levy et al. 1996) For such chronic or long term pathologic conditions, administration may need to be extended for a period of years.

Immune Modulation: Low dose poly-ICLC has a complex, direct immune modulating action at times relatively independent of interferon, including T-cell and natural killer cell activation, endothelial, respiratory epithelial, astrocytic, and myeloid dendritic cell (DC) activation via Toll-like receptors 3 and 7 (see below), induction of a "natural mix" of cytokines (e.g. interferons alpha, beta, and gamma, interleukins, chemokines, corticosteroids, and TNF), and a potent adjuvant effect with increased antibody response to antigen. (Levy and Bever 1988) The complex interactions of the dsRNAs and the interferons in this regard are as yet incompletely understood, but they can still be used to clinical advantage in several different settings, including vaccination and autoimmune disease as well as certain cancers or viral infections that inhibit the immune system. For example, although preliminary laboratory results in our pilot study in brain tumor patients showed no clear relationship between tumor response and measurable serum interferon, TNF, IL2, IL6, or neopterin, a peritumoral inflammatory response has been pathologically documented after poly-ICLC treatment of brain tumor patients, suggesting that its therapeutic effect may be at least partly mediated by its immunomodulatory as well as by its antiproliferative actions. This is further supported by data to be presented showing extended survival of glioblastoma patients with an inflammatory MRI peri-tumoral lesion enhancement during a several month course of poly-ICLC.

Clinical Reversal or Preemption of Viral and Neoplasm-Induced Immunosuppression by Poly-ICLC.

Ebola Virus: One example of a highly pathogenic virus that thrives by inhibiting host defenses is the Ebola virus. Preclinical and clinical studies of Ebola virus infection have shown that its lethality is largely related to its ability to evade various elements of both innate and adaptive immunity. These include evasion of the interferon (IFN) system, IFN regulatory factor, the dsRNA dependent protein kinase (PKR) and 2'5' OAS, NK cells and macrophages; as well as inhibition of dendritic cells, MHC I, various cytokines such as IL-6, and TNF, and other elements of adaptive immunity. (Warfield, J G et al. 2004), (Bosio, Aman et al. 2003) (Geisbert, Hensley et al. 2003) (Gibb, Norwood et al. 2002). (Harcourt, Sanchez et al. 1998). This inhibition eventually precipitates a cascade of failure of host defenses resulting in full-blown disease with up to 90% mortality. Significantly, however, the inhibition does not appear to begin until more than 24 hours after infection, suggesting that there is a significant peri-exposure window within which exogenous activation of innate immunity can provide protection. This prediction is consistent with our very recent, unpublished preclinical findings to be presented showing marked protection by poly-ICLC from viral challenge with Ebola-Zaire virus. (Kende, et al) Likewise, poly-ICLC provides similar protection against vaccinia virus, which also suppresses dendritic cells via the A52R protein.

Another example of the therapeutic potential of immunomodulation with poly-ICLC is its use to protect the respiratory, gastrointestinal and genital mucosal portals of infection as discussed below.

Finally, as further discussed below, many neoplasms or neoplastic factors will also directly inhibit dendritic cells or other elements of adaptive immunity. This is emerging as a major factor in the repeated failure of vaccination strategies for treatment of various cancers. We will present additional data to demonstrate that poly-ICLC will preempt or reverse this inhibition clinically, as well as in vitro, which may be an additional mechanism of its antitumor action when administered either alone, or in combination with vaccine and/or other drugs.

Autoimmune Disease, Multiple Sclerosis

Figure 7:
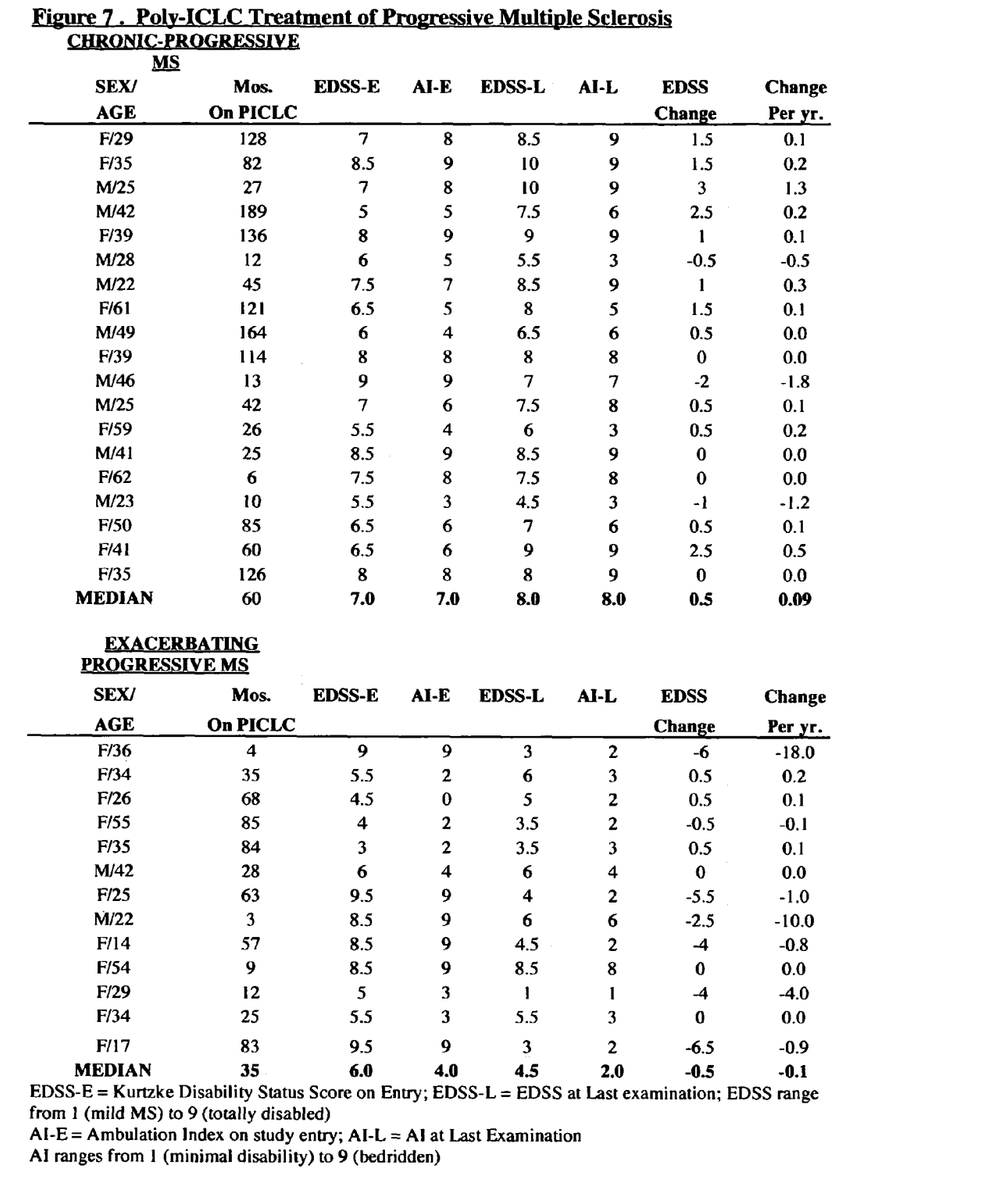
FIG. 7 is an unpublished table showing low dose, long term IM poly-ICLC treatment of Progressive Multiple Sclerosis, showing relative stabilization and or improvement of neurological status. This is possibly mediated by poly-ICLC modulation of interferon, MHC expression, and/or Treg cells. (Please see Examples B, page 31.)

The immunomodulatory effect of long-term, low-dose poly-ICLC includes activation of certain immune elements involved in the discrimination between self and non-self. This includes myeloid dendritic cell activation via TLR-3, increased MHC expression as well as modulation of certain regulatory T4 cells (CD4+CD25+ or T reg cells). Modulation of these systems may be an important mechanism mediating the benefit seen in treatment of multiple sclerosis patients with low dose, long-term IM poly-ICLC. (Salazar, et al, unpublished) This is in contrast to mixed results and increased toxicity seen in our previous trial of high dose IV poly-ICLC. (Bever, Salazar et al. 1986) This is further discussed below and demonstrated in FIG. 7. Additional data will be presented demonstrating the clinical modulation of T reg cells by Poly-ICLC. Other chronic autoimmune conditions are similarly expected to respond to low dose poly-ICLC therapy as described here.

Vaccine Adjuvant Use of Poly-ICLC and Other PAMPs

Attempts to induce the body to mount a protective or immune defense against disease have captured the medical imagination for centuries, from the practice of variolation to prevent smallpox well over a thousand years ago in China, to the use of modern dendritic cell and DNA vaccines. Yet even these latter remain imperfect tools for inducing an effective immune response against many pathogens or tumors; the reasons for these failures are multiple (Desrosiers 2004), (Buteau, Svetomir et al. 2002) (Rosenberg, Yang et al. 2004)

Vaccines have been used not only to prevent disease, but also in a therapeutic mode to enhance the body's defenses against existing disease. Specific examples include the use of therapeutic vaccines to treat HIV infection or neoplastic disease. However, it has also become apparent that many of the mechanisms that have evolved to protect the body from disease are themselves subjected to inhibition by various pathogens. We now recognize that not only can certain viruses such as HIV infect immune cells directly, but both viral and neoplastic products can also suppress other key elements of both the innate and adaptive immune responses.

The use of dsRNAs and poly-ICLC in particular as immune adjuvants has been described in the older experimental literature, (Stephen, Hilmas et al. 1977) (Levy and Bever 1988) but this has not yet led to practical clinical applications. However, as noted above, recent studies have shed further light on the potential mechanisms of action of PAMPs and suggested a new approach to their use as adjuvants.

One important signaling pathway of the innate immune response involves recognition of dsRNA or other PAMPS by various cell surface pattern recognition receptors (PRR), among the most important of which now appear to be the RIG-I system and Toll-like receptors (TLR) (Iwasaki and Medzhitov 2004). This initiates a complex signaling cascade leading to various cellular changes, including altered expression of various interferons, cytokines, chemokines and other costimulatory molecules and transcription factors such as NFkB, cJun, IRF3, and ATF2. (Sen and Sarkar 2005) The TLR system is thus currently seen as one of the critical links between innate and adaptive immunity.

Figure 5:
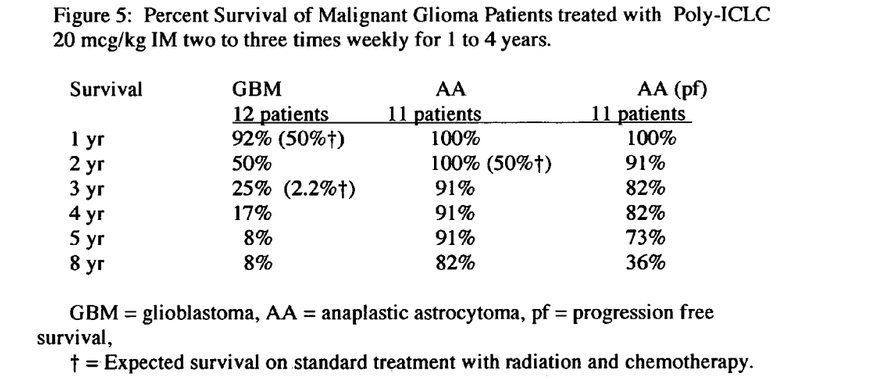
FIG. 5 is a table demonstrating markedly increased survival of malignant glioma patients treated with 20 mcg/kg poly-ICLC IM, plus chemotherapy, using the repeated dosing regimen described two to three times weekly for up to 4 years. This effect is mediated by activation of various elements of innate immunity by the poly-ICLC. This protection involves both antiproliferative mechanisms involving reactivation of OAS and PKR, as discussed above, as well as induction and maintenance of an adaptive immune response to tumor cells. Induction of an immune response to tumor antigens released by chemotherapy is facilitated by TLR3 and other dsRNA signaling on immune cells, while maintenance and targeting may also be facilitated by TLR3 receptors on cerebral glia and tumor cells as well as vascular endothelial cells.

There are a number of different Toll-like receptors (TLRs) responding to different PAMPs. DsRNAs activate TLR-3, while TLR 7 responds to ssRNA and TLR 4 and 9 respond to bacterial or DNA PAMPS such as lipopolysaccharide and CpG. While some of the signaling pathways are shared, the differential activation of TLRs appears to trigger host responses that are specialized to address particular pathogen subtypes, including neoplasms. TLR-3 are found intracellularly in myeloid dendritic cells, which induce a Th1 or cellular immune response that is especially adapted to defense against many viruses as well as some cancers. They are also found on respiratory epithelium, vascular endothelium, and brain astrocytes, which may have an impact on the integrity of the blood brain barrier. TLR3 are also expressed on the surface some some glial tumors, which may also have implications for immune targeting of these neoplasms and the mechanism of the beneficial effect that we have seen, as illustrated in FIG. 5.

Treatment with combinations of different PAMPs leading to activation of multiple TLRs may be expected to result in a more potent, albeit not necessarily more specific immune response. For example, while dsRNA binds to and activates TLR-3, simultaneous activation of TLR 9 by CpG motifs potentiates the innate and adaptive response. However, chronic stimulation of TLR-9 with CPG can be toxic, unlike similar stimulation of TLR-3 with poly-IC. (Heikenwalder, Polymenidou et al. 2004). Also, different TLRs show cross talk with each other. For example, while dsRNA activates TLR3, there may be components of the poly-ICLC complex that are single stranded and have the capacity to activate TLR7, which recognizes single stranded RNA from several virus species. Thus influencing more than one TLR could provide an advantage in treatment of certain weakly immunogenic pathogens. On the other hand, the more specific binding of poly-ICLC to TLR-3 may be preferable when a more targeted cytotoxic T-cell response is desired.

Cytotoxic T lymphocytes (CD8+, CTL) are a major host defense mechanism against viral infection and cancer. CD8+ CTL recognize and lyse virus-infected cells following binding of the T cell receptor to a viral or neoplastic antigen presented in the context of MHC molecules. The HLA type of an individual thus plays a major role in determining whether they will generate a CTL response to a given epitope. The specific binding of poly-IC to TLR-3 is more effective at activating myeloid derived DC, which favor a particular cytotoxic T-cell response.

Mature DC are among the most potent antigen presenting cells (APC) and activators of CTLs. (Fujimoto, Nakagawa et al. 2004), (Verjdijk, Mutis et al. 1999; Datta, Redecke et al. 2003)) In vivo, this process requires at least 24 hours and ideally involves not only the direct effect of the PAMP on DC TLRs, but also its concomitant induction of interferon and a "natural mix" of other cytokines, chemokines, and costimulatory molecules, as well as its induction of MHC I and II. (Mattei, Schiavoni et al. 2001), (Ponsaerts, Van den Bosch et al. 2002), (Honda, Sakaguchi et al. 2003)) Thus, DC that have been non-specifically "primed" through activation with a TLR agonist such as poly-ICLC alone prior to antigen exposure will be much more responsive to antigen and more efficient mediators of both cell mediated and humoral immunity. This can be achieved clinically by pretreatment with a poly-ICLC or certain other viral mimics or PAMPs alone at about the time of antigen presentation.

Therapeutic Vaccination: The activation of myeloid DC by dsRNAs such as poly-ICLC is especially important when one is administering vaccine in treatment of established chronic infection or neoplasm. As noted above, many viruses and neoplasms will inhibit DC through various mechanisms. Reversal of this inhibition by priming with PAMPs such as poly-ICLC would be expected to maximize DC action and efficiency of vaccine antigen processing, including management of MHC and distinction of non-self from self antigens. This process might be expected to take at least 12-24 hours to several weeks, and may also require repeated treatments with poly-ICLC, depending on the chronicity of the disease in question. On the other hand exposure to poly-ICLC longer than 48 hours prior to antigen presentation may also be less efficient (Spisek, Bougras et al. 2003)) Poly-ICLC is particularly expected to improve host defenses requiring a Th1 response, such as viral infection and neoplastic disease. (de-Jong'02) Data will be presented demonstrating marked enhancement by poly-ICLC of DC maturation, MHC and costimulatory molecule expression as well as T4 cell and CTL cell activation in both preclinical and clinical settings.

Cancer Vaccines

One vexing challenge in the vaccine field is the development of therapeutic cancer vaccines. Many of the obstacles to development of an effective cancer vaccine have been discussed elsewhere. They include epitope identification and selection, relative lack of immunogenicity of vaccines, development of immune tolerance by the host, MHC restriction, development of tumor escape mutants, and other immune evasion by tumor cells (Buteau, Svetomir et al. 2002). This latter includes suppression of MHC and surface antigen expression, as well as inhibition of dendritic cell maturation and function by multiple tumor products, as noted previously above. (Shurin, Shurin et al. 2001), (Autran, Carcelain et al. 2004), (Kaufman and Disis 2004)) Among these are prostate specific antigen (Aalamian, Tourkova et al. 2003), tumor-derived IL-10; and neuroblastoma-derived gangliosides (Shurin, Shurin et al. 2001). A clinical methodology as presented here, utilizing Poly-ICLC and/or other related dsRNAs or PAMPs to reverse or preempt this inhibition could be of major therapeutic significance. Data will be presented to demonstrate this reversal of tumor induced inhibition by poly-ICLC both in-vitro and clinically. Since submission of the provisional version of this application, additional data has been published demonstrating this enhancement of tumor specific cytotoxic lymphocytes in response to cancer vaccine administered with plain poly-IC in mice (Salem, Kadima et al. 2005). However, a stabilized dsRNA such as Poly-ICLC would be required to elicit a comparable response in primates and man T-regulatory cells (CD4+, CD25+ or T-reg) are involved in policing the distinction between self and non-self antigens, and may represent another of the important mechanisms suppressing the immune response to many cancers. Strategies that minimize the action of T-reg cells would thus be expected to facilitate the immune response to tumors. (Sutmuller, van Duivernvoorde et al. 2001). One such example is use of the drugs cytoxan or temozolomide (TMZ), which in addition to their tumoricidal action, also preferentially deplete T-reg cells (Su, Sohn et al. 2004). When properly timed, the combination of drugs such as TMZ with poly-ICLC and/or vaccine would be expected to further enhance the generation and effectiveness of tumor-specific cytotoxic lymphocytes. Ideally, in this case poly-ICLC would be administered with or without tumor vaccine antigen following a course of a drug such as TMZ.

HIV Infection and HIV Vaccination Strategy:

Another example of the challenges in the field is human immunodeficiency virus (HIV) infection. Obstacles to the development of an effective AIDS vaccine include factors related to the biology of HIV-1 infection and practical realities of developing and testing an AIDS vaccine. These include increased sequence variation, lack of information regarding specific nature of HIV protective immunity, eg, the roles of neutralizing antibody, and CTL at the various stages of infection and replication. Despite intensive study, however, there is no definitive information about the correlates of protective immunity. Consequently, most investigators believe that a successful AIDS vaccine should be able to induce both HIV-specific CTL and neutralizing antibody responses. Most HIV-infected individuals develop a relatively strong virus-specific CD4+, and CD8+ CTL response, as measured by a variety of in vitro assays. However, this response is qualitatively inadequate in most HIV infected patients and is characterized by HIV-specific but monofunctional T cells that secrete mostly IFN gamma. In contrast, T cells from HIV-infected, yet long-term non-progressor patients are polyfunctional, with a balanced interferon gamma (IFNg) and interleukin 2 (IL-2 secretion). Similarly, patients undergoing successful HIV antiviral therapy will revert from a monofunctional to a polyfunctional T-cell profile, further suggesting that the quality of the T-cell response is an important element in HIV pathogenesis. (Harari, Petitpierre et al. 2004), (Pantaleo and Koup 2004). As a demonstrated inducer of IL-2, poly-ICLC is expected to help restore a polyfunctional T-Cell profile, which may be especially important in a therapeutic vaccination setting. In related findings, others have very recently demonstrated that poly-IC will enhance the quality of the immune response to influenza vaccine by broadening cross-strain protection. This is likely related to an enhanced cellular immunity and may also be relatively independent of IFN gamma. (Ichinohe, Watanabe et al. 2005)

In a pilot trial of poly-ICLC with or without Zidovudine in advanced AIDS patients, we have demonstrated encouraging stabilization or increases in T4 and T8 cells along with a trend towards decreasing viral load (see FIG. 4) This finding further supports the potential role of poly-ICLC, not only as an antiviral agent, but also as a potential adjuvant to AIDS vaccines.

Mucosal Vaccination: Role of Poly-ICLC.

Figure 2:
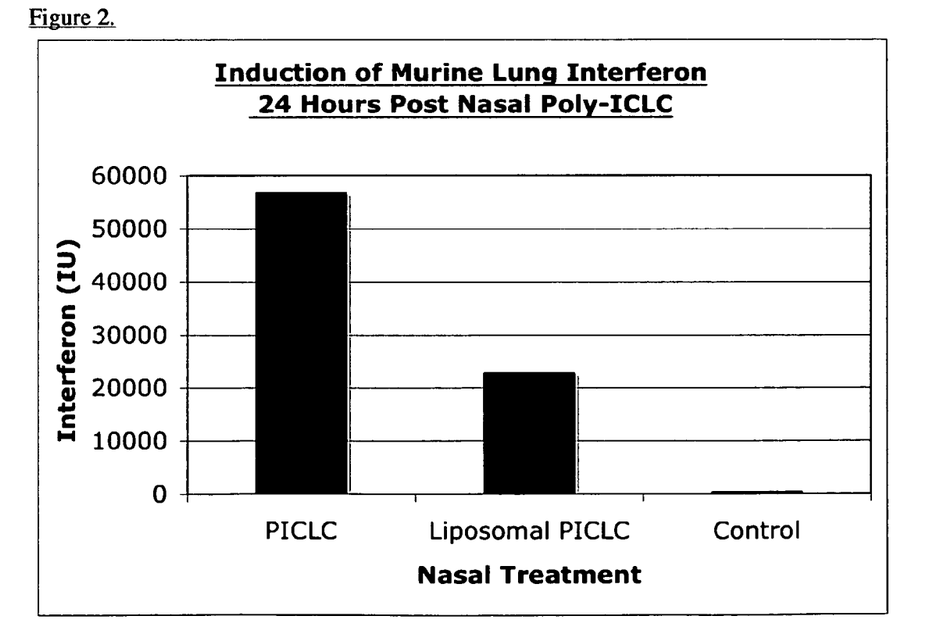
FIG. 2 is a chart demonstrating robust induction of lung interferon by nasally administered poly-ICLC and liposomal poly-ICLC in mice, also indicating activation of iBALT.

Mucosa, as a potential first portal of entry of many foreign antigens that may be pathogenic (eg microbes) as well as non-pathogenic (eg foods), has developed a relatively unique immune system that is necessarily separate from systemic immunity. The inducible mucosal associated lymphoid tissue (iMALT, also known as iNALT iBALT, or iGALT in the nasal, bronchial, or gastrointestinal mucosa respectively) is thus a self contained and relatively isolated portion of the host defense that may account for as much as 80% of the immune system and that is also particularly concerned with distinction between self and non-self. Reviewed in (Holmgren and Czerkinsky 2005). Activation of iBALT with nasally applied poly-ICLC can provide marked protection in certain important diseases. For example intranasal treatment with poly-ICLC or liposomal poly-ICLC can provide protection for as long as three weeks in an otherwise lethal model of murine influenza (Wong, Saravolac et al. 1995) (see also Wong U.S. Pat. No. 6,468,558). We now have demonstrated that nasal application of plain poly-ICLC in monkeys will result in a robust host defense activation manifested by induction of serum interferon. (See FIG. 2). Similar experiments have demonstrated interferon induction in the lung tissue of mice treated with nasal poly-ICLC. (FIG. 3) Since submission of the provisional version of this patent application, additional evidence has been published confirming these findings. (Ichinohe, Watanabe et al. 2005)

Not only is the iMALT relatively isolated from systemic immunity, but mucosa in different locations also have their own specific immune attributes and cross protection. Immunization of the mucosal portals is thus a very effective method of protecting against a number of pathogens. Successful examples include mucosal vaccines against polio, cholera, typhoid, and influenza, which tend to stimulate a humoral response. Increasing evidence also points to vaginal and gastrointestinal mucosal lymphoid tissue as the site of initial HIV infection and explosive viral replication suggesting that mucosal vaccination may be the optimal strategy for containment of this disease.

However, as noted above, the challenges facing vaccine development for certain chronic pathogenic viruses such as HIV include stimulation of a Th1 or cellular immune response, as well as a Th2 or neutralizing antibody response. DsRNAs, partly by virtue of their activation of myeloid DC via TLR3 are especially well suited for this purpose. For example we have now demonstrated iMALT activation by nasal poly-ICLC as evidenced by stimulation of a robust interferon response in the lung and serum in mice and monkeys. (FIGS. 6 and 7) However, excessive doses of poly-ICLC in the face of a viral or antigenic challenge can also be counterproductive if they generate an excessive inflammatory response, even if those doses also result in decreased viral titers. Likewise, the adjuvant effect of poly-ICLC at the time of vaccination will be optimal if it is administered in a modest dose to a relatively naïve host (ie. if it is given either for the first time or after at least a several day holiday from previous administrations)

Since submission of our provisional patent, others have also very recently also demonstrated iMALT TLR activation by plain poly-IC in mice. There is also now evidence that iNALT activation crosses over to protection of vaginal mucosa. Taken together, this suggests that poly-ICLC can be a potent adjuvant for logistically simple intranasal vaccines directed at containment of epidemics of sexually transmitted diseases such as HIV that require a cellular immune response. As with systemic immunization dosage and timing of Poly-ICLC administration in relation to vaccine antigen can be critical. Additional data supporting this adjuvant action in primates will be presented.

Poly-ICLC as an Adjuvant for Live Virus and Vector Vaccines

The seemingly paradoxical dual role of poly-ICLC as an antiviral agent and vaccine adjuvant is consistent with its function as a viral-mimic in establishing an immediate innate defense system against viral attack while at the same time facilitating the development of long term immunity, Poly-ICLC thus provides a link between innate and adaptive immunity, possibly through early activation of TLRs on dendritic cells and an improved efficiency of antigen processing and T-cell activation. Thus, in contrast to conventional antiviral agents, poly-ICLC could represent an ideal adjuvant to certain live virus vaccines, especially those such as smallpox vaccine that carry significant morbidity related to uncontrolled vaccine virus proliferation, or for certain vector vaccines that are only able to elicit a weak or qualitatively inadequate immune response. (Pantaleo and Koup 2004)

We have demonstrated that poly-ICLC does not interfere with the immunity provided by smallpox vaccine (Dryvax) in mice and monkeys, as measured by antibody response and resistance to viral rechallenge. (Baron, Salazar et al, unpublished, 2003, 2004) See FIG. 4.

Modifications to the Structure of Poly-ICLC

Poly-ICLC is a large molecule stimulating a broad spectrum of host defenses.

The mechanisms underlying immune activation, tolerance, and the interaction between innate and adaptive immunity are only now beginning to be better understood. This is particularly so of the critical role that TLR activators such as poly-ICLC, other dsRNAs and PAMPs appear to play in bridging the two arms of the host defense. As noted above, the interplay between different TLRs, as well as the differential activation of a specific TLR, (such as that of TLR-3 by different dsRNA species) may have an important clinical role, possibly by more precisely targeting the response to a particular pathogen or neoplasm, and by fine tuning the critical distinctions between self and non-self. Additionally, certain elements of the potent broad-spectrum host response to a relatively simple unmodified viral mimic such as poly-ICLC may be more desirable in some clinical situations and less so or undesirable in others In this context, modifications to the structure of dsRNA may provide certain clinical advantages in the management of particular pathologies. This was recognized years ago as researchers worked to develop modifications to dsRNA species, including terminal and structural modifications using phosphorothioate linkages, alterations in the relative ratios of or in the size of poly I to poly C in the dsRNA constructs, nucleotide mismatches as in Ampligen, the search for stabilizing modifications, with the ultimate selection of poly-1-lysine and/or dextran, alterations to the size of the poly-lysine, and others. (Morahan, 1972), (Levy 1986)

An additional advantage to developing alternative and smaller molecules may be the potential increased ease of manufacture using modern automated synthesis technologies, as well as concomitant reduction in cost.

Finally, we have found a differential effect on gene regulation between poly-IC and poly-ICLC. Alternative dsRNA or PAMP structures may thus serve to modulate the immune system in different ways that are better suited to treatment of a particular disease entity. Additional modifications would be expected to expand or restrict the spectrum of activation of various TLR or even the response to activation of a particular TLR, possibly through differential activation of costimulatory molecules. Data will be presented demonstrating the differential antiviral and immunomodulatory activity of several of these molecular variations on poly-ICLC

SUMMARY OF THE INVENTION

The foregoing problems are overcome, and other advantages are provided by an improved, non-toxic method for utilizing poly-ICLC and certain other PAMPs in humans clinically, intranasally, topically, orally, mucosally, intravenously, transdermally, subcutaneously and/or intramuscularly to modulate the immune system for treatment of certain neoplastic, infectious and autoimmune conditions. It is a further object of the invention to provide an improved method for administration of poly-ICLC that results in markedly decreased toxicity, and marked enhancement of its clinical and veterinary uses and its multidimensional biological effects In accordance with the first aspect of the invention, is an improved, non-toxic method for utilizing poly-ICLC clinically in humans as above to increase resistance to a broad variety of viral and other infections that thrive by inhibiting the immune system, to thereby provide for containment of epidemic outbreaks of such infections with or without concomitant vaccination or other drugs; including but not limited to viral influenza, smallpox, SARS, RSV, Hepatitis, and Ebola infection in humans or animals as well as veterinary viral infection including but not limited Bovine respiratory complex, influenza, and foot and mouth disease.

In accordance with a second aspect of the invention, is an improved, non-toxic method for utilizing poly-ICLC clinically in humans as above to enhance the action and/or decrease the toxicity of various preventive or therapeutic vaccines, including live virus vaccines, subunit vaccines, dendritic cell vaccines, peptide-based and other vaccines designed to stimulate either systemic or mucosal immunity.

In accordance with a third aspect of the invention, an improved method of administration of poly-ICLC (intranasally, orally, sublingually, intramuscularly, intravenously subcutaneously, topically, or with dermal patch or transdermal vehicle) comprises administration in at least two doses spaced 4-72 hours apart, where the first dose is either mixed with vaccine or separately in the same limb or location and at about the time of administration of the viral or cancer vaccine containing the target antigen, and is administered in a moderate range (10 to 100 mcg/kg in humans) sufficient to induce a "natural mix" of interferons, cytokines, chemokines costimulatory molecules, enzymes such as OAS and PKR, PRR such as TLR3, and other regulatory molecules such as p56; and the subsequent doses are administered alone to stimulate or disinhibit the induced enzymes such as OAS and PKR, or PRRs such as TLR3 and continue the dendritic and T-cell maturation and tumor targeting process. This approach may be extended to the use of other dsRNAs to achieve similar results. When used in this manner to enhance the activity of therapeutic vaccines, poly-ICLC and other dsRNAs may need to be continually administered every two to three days as described over a period of at least two days to two weeks or more (months to several years), depending on the extent of tumor or chronicity of the viral induced immune dysfunction.

In the case of chronic viral infections or neoplasms that inhibit the immune system, poly-ICLC may be administered every two to three days for two to three weeks prior to administration of poly-ICLC plus vaccine, as above, except that there should be an interval of at least 2 to 5 days since the last poly-ICLC administration and the actual vaccination combination. When properly administered, poly-ICLC will thus enhance both the immune-induction and the effector or pathogen-targeting phases of therapeutic vaccination.

When protection of a mucosal portal of infection is desired, or for certain autoimmune conditions, one or more of the dosages and vaccine may also be delivered mucosally. (See section II under Preferred Embodiments)

It is a further object of the invention to provide an improved method for use of poly-ICLC in the management of autoimmune conditions, including multiple sclerosis.

Further applications include similar regulation of immune responses for veterinary applications in various mammalian animal species, poultry, and other birds.

It is a further object of the invention to provide a concept for developing alternative dsRNA structures that result in differential immunomodulatory, gene regulatory and other biological effects that can be tailored to specific disease entities.

BRIEF DESCRIPTION OF THE DRAWINGS

Briefer periods of exposure may not be sufficient to induce a proper response. This implies that for clinical use in humans or for veterinary applications, a practical aerosol or spray formulation that ensures such prolonged exposure may be necessary for adequate protection of the respiratory portal.

DESCRIPTION OF THE PREFERRED EMBODIMENTS

I. Phased Multi-Dose Treatment

The complex interaction of the interferons and dsRNA-activated systems can be manipulated to therapeutic advantage, particularly in the case of those certain microbial and neoplastic diseases that thrive by circumventing certain host defense mechanisms involving both innate immunity (eg OAS and the PKR) and adaptive immunity. Poly-ICLC should be administered intramuscularly or subcutaneously locally in the same limb as vaccine, in order to stimulate local dendritic cell trafficking. Administration in a remote site will be much less effective or ineffective. Poly-ICLC can also be administered orally or mucosally including nasally at about the time of vaccine administration or mixed with vaccine in order to achieve the desired adjuvant effect. Clinical data will be presented to support this claim.

Figure 1:
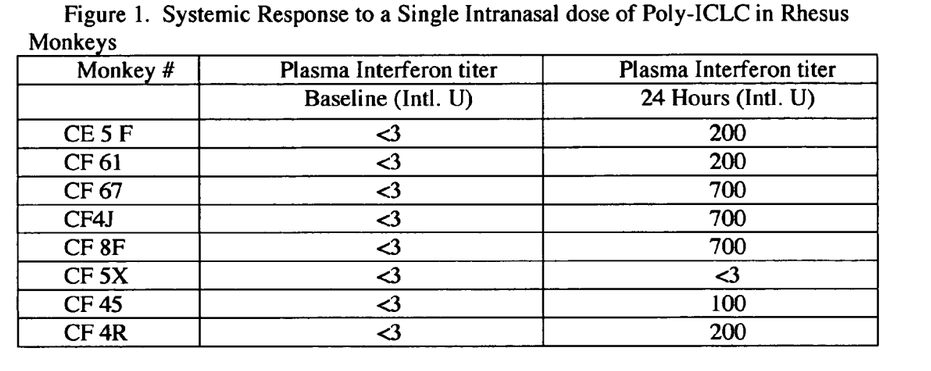
FIG. 1 is a table showing Systemic Response to intranasal administration of poly-ICLC in Rhesus Monkeys, indicating activation of iBALT. One consideration is the duration of exposure of the nasal and bronchial mucosa to poly-ICLC or other dsRNAs. Animals were anesthetized prior to nasal administration, ensuring exposure of the full dose for at least 30 minutes to mucosal surfaces.

Clinical trials of poly-ICLC to date have utilized the intravenous (IV) or intramuscular (IM) routes of administration. Wong and others have demonstrated that intranasal poly-ICLC can protect from nasal viral challenge in anesthetized mice. We have now have demonstrated that intranasal treatment of non-human primates (rhesus monkeys) with poly-ICLC will also result in a robust systemic response as measured by plasma interferon at 24 hours, but not 8 hours from administration, as shown in FIG. 1. This unexpected result opens the possibility of using intranasal, sublingual, or topical poly-ICLC for treatment of systemic diseases. This may be especially advantageous in long term treatment of cancer or autoimmune diseases, treatment of large number of individuals exposed to HIV or a bioterror threat such as smallpox; or for veterinary use, as in containment of an outbreak of foot and mouth disease in cattle, management of the bovine respiratory complex, avian influenza, or respiratory syncytial virus infection. However, as noted above, one consideration is the duration of exposure of the nasal and bronchial mucosa to poly-ICLC. The animals treated in the experiment illustrated in FIG. 1 were anesthetized prior to nasal administration, ensuring exposure of the full dose for at least 30 minutes to mucosal surfaces. This implies that for clinical use in humans or for veterinary applications, a practical aerosol or spray formulation that ensures such prolonged mucosal exposure may be necessary for adequate protection of the respiratory portal.

Similarly, based on the experience with oral interferon use, it is also hypothesized that orally or sublingually administered poly-ICLC may be sufficient to yield a clinical therapeutic response. Oral administration in a suitable formulation could also be especially advantageous in large-scale human or veterinary uses. Finally, older rabbit studies demonstrated protection from vaccinia by topically administered poly-ICLC. This suggests that topical administration of poly-ICLC in a dermatologic preparation or dermal patch may also be efficacious for certain applications in humans. (Levy and Lvovsky 1978) Further data will be presented to support these claims.

II. Examples

An Improved Method for the Clinical And Veterinary Immunomodulatory or Adjuvant Use of poly-ICLC It is expected that poly-ICLC would have application to the treatment of a variety of diseases including certain neoplastic, infectious, and autoimmune disorders.

The following examples are illustrations, but not limitations, of the approach. Given these examples, one of ordinary skill in the art could apply the same approach to other diseases.

A) Example of Clinical Treatment of a Retroviral Disease: Treatment of AIDS with poly-ICLC. In an open pilot trial, low dose (0.2-2 mg) poly-ICLC was administered intramuscularly (IM) 1-3 times per week with or without Zidovudine over up to 30 months to 22 patients with HIV infection or AIDS. (Salazar, Morales et al. 1990) poly-ICLC was well tolerated, with no significant clinical or laboratory toxicity. Side effects consisted of a mild 12-24 hour flu-like syndrome with low-grade fever and malaise at the higher doses, but usually disappeared after the first half-dozen treatments. 12/20 patients showed at times dramatic initial rises in T4 cell counts along with symptomatic improvement, although this was not uniformly maintained. Plasma P-24 titers (a measure of viral load), which were positive in 8/16 patients before biweekly treatment, either became undetectable or remained so in all but one patient, whose titers were markedly elevated at onset and dropped by 75% with treatment.

In a separate dosing study of poly-ICLC in 8 AIDS patients, neuropsychological testing has shown a marked improvement in choice reaction time and the Purdue pegboard test at 16 weeks of treatment, with a deterioration back to baseline when poly-ICLC was discontinued. This contrasts with a gradual, statistically significant deterioration in choice reaction time seen in an untreated HIV+ cohort (N=41) over six months. As suggested above, it is expected that even better responses than those seen to date may be achievable utilizing the new double-dosing technique described in Section B, above, and shown in FIG. 5.

B) Example of poly-ICLC Treatment of an Autoimmune Disorder: Treatment of Multiple Sclerosis This and other considerations led us to an open trial of high dose (100 mcg/kg) intravenous poly-ICLC showed moderately severe acute toxicity in 15 patients with chronic MS; several patients improved or stabilized, but deteriorated when drug was stopped, as reported by Bever, Salazar, et al., 1986. (Bever, Salazar et al. 1986) Subsequently, Salazar continued to treat some of these and other MS patients with a completely new extended regimen using much lower doses of poly-ICLC intramuscularly over a longer period of time. Results of this follow-up study are unpublished, and are disclosed below.

Methods: Thirty one patients with either chronic progressive (CP) or exacerbating progressive (EP) multiple sclerosis received 5-100 mcgm/kg PICLC IM q 3-14 days for up to 15 years; most received a median dose of 10 mcg/kg weekly.

Figure 6:
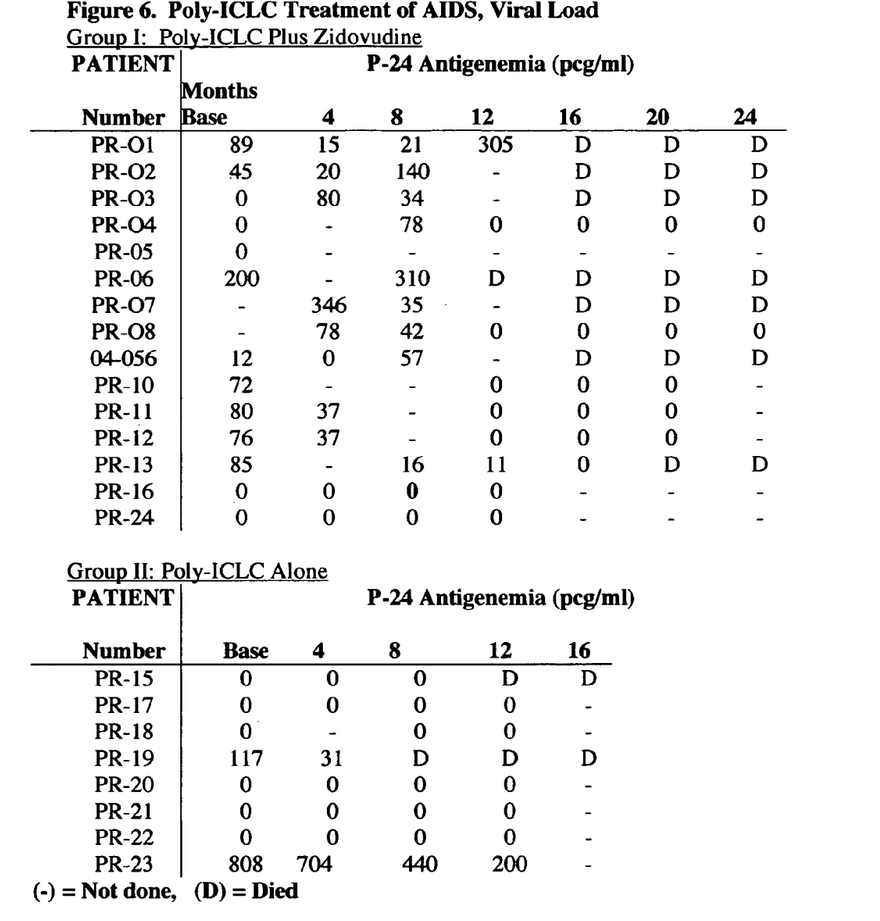
FIG. 6 is a table showing decrease or stabilization of HIV viral load in blood after treatment of advanced AIDS patients with low dose, long term poly-ICLC. Additional data in the same patients shows stabilization or improvement of T4 cell counts, indicating at least partial reversal of viral induced immunosuppression. (Please see Example A, page 30)

Toxicity was markedly reduced to an inconstant, mild, transient malaise. The Kurtzke Expanded Disability Status Score (EDSS, which varies between 0 (normal) and 9 (totally bedridden and dependent) was used to evaluate outcome. As shown in FIG. 6, the EDSS remained stable or improved in 15/31 patients (dramatically in 5). Six patients deteriorated when poly-ICLC was stopped. The 19 CP patients showed a median EDSS change of 0.09 points per year over a median of 60 months; while the 12 EP patients showed a slight improvement (−0.1 EDSS per year) over a median of 28 months. These rates compare very favorably with the expected rates of progression in untreated multiple sclerosis patients. (Note that a lower Kurtzke score is better).

Therefore, IM low dose poly-ICLC may be a valuable alternative to the more expensive and toxic beta-interferons for long-term management of MS. As suggested above, it is expected that even better response rates than those seen to date may be achievable utilizing the new double-dosing technique described above.

C) Example of Reversal of Viral and Tumor Induced Inhibition of Dendritic Cells with poly-ICLC and other PAMPs Additional data will be presented to demonstrate the prevention as well as reversal of tumor-induced inhibition of dendritic cells either in vivo or in vitro by treatment of cell cultures and/or cancer patients with poly-ICLC and certain other dsRNAs. In vitro studies will demonstrate preemption/reversal of DC inhibition by prostate specific antigen. Clinical trials in patients with advanced prostatic cancer will demonstrate in-vivo reversal of DC inhibition and enhanced CTL response to a prostate cancer antigen based vaccine in response to poly-ICLC priming and treatment as described herein.

REFERENCES

Aalamian, M., I. Tourkova, et al. (2003). "Inhibition of dendropoesis by tumor derived and purified prostate specific antigen." *J Urology* 170(11): 2026-2030.

Autran, B., G. Carcelain, et al. (2004). "Therapeutic vaccines for chronic infections." *Science* 305: 205-212.

Bever, C., A. Salazar, et al. (1986). "Preliminary trial of poly-ICLC in chronic progressive multiple sclerosis." *Neurology* 36(4): 489-493.

Bosio, C., M. Aman, et al. (2003). "Ebola and Marburg viruses replicate in monocyte-derived dendritic cells without inducing the production of cytokines and full maturation." *J Infect Dis* 188(11): 1630-8.

Buteau, C., S N, N. Svetomir, et al. (2002). "Challenges in the development of effective peptide vaccines for cancer." *Mayo Clin Proc.* 77: 339-349.

Datta, S., V. Redecke, et al. (2003). "A subset of Toll-like receptor ligands induces cross-presentation by bone marrow derived dendritic cells." *Journal of Immunology* 170: 4102-4110.

Desrosiers, R. (2004). "Prospects for an AIDS vaccine." *Nature Medicine* 10(3): 221-223.

Fujimoto, C., Y. Nakagawa, et al. (2004). "Polyriboinosinic polyribocytidylic acid TLR3 signaling allows class I processing of exogenous protein and induction of HIV-specific CD8+ cytotoxic T lymphocytes." *International Immunology* 16(1): 55-63.

Galabru, J., M. Katze, et al. (1989). "The binding of dsRNA and adenovirus VA1 RNA to the interferon-induced protein kinase." *European Journal of Biochemistry* 178: 581-89.

Geisbert, T., L. Hensley, et al. (2003). "Pathogenesis of Ebola hemorrhagic fever in conomolgus macaques: evidence that dendritic cells are early and sustained targets of infection." *Am J Pathol* 163(6): 2347-70.

Geiss, G., G. Jin, et al. (2001). "A comprehensive view of regulatio of gene expression by double-stranded RNA-mediated cell signaling." *J Biol Chem* 276(32): 30178-30182.

Gibb, T., D. Norwood, et al. (2002). "Viral replication and host gene expression in alveolar macrophages infected with ebola virus-Zaire." *Clin Diag Lab Immunol* 9(1): 19-27.

Harari, A., Petitpierre, et al. (2004). "Skewed representation fo functionally dinstinct populations of virus-specific CD4 T cells in HIV-1 infected subjects with progressive disease: changes after antiretroviral therapy." *Blood* 103(3): 966-972.

Harcourt, B., A. Sanchez, et al. (1998). "Ebola virus inhibits induction of genes by dsRNA in endothelial cells." *Virology* 252: 179-188.

Heikenwalder, M., M. Polymenidou, et al. (2004). "Lymphoid follicle destruction and immunosuppression after repeated CpG oligodeoxynucleotide administration." *Nature Medicine* 10(2): 187-192.

Holmgren, J. and C. Czerkinsky (2005). "Mucosal immunity and vaccines." *Nat Med* 11(4): 545-553.

Honda, K., S. Sakaguchi, et al. (2003). "Selective contribution of IFN alpha beta signaling to the maturation of dendritic cells induced by dsRNA or viral infection." *PNAS* 100(19): 110872-10877.

Ichinohe, T., I. Watanabe, et al. (2005). "Synthetic dsRNA Poly(I:C) combined with mucosal vaccine protects against influenza virus infection." *Journal of Virology* 79(5): 2910-2919.

Iwasaki, A. and R. Medzhitov (2004). "Toll-like receptor control of the adaptive immune responses." *Nature Immunology* 5(10): 987-995.

Jacobs, B. and J. Langland (1996). "When two strands are better than one: the mediators and modulators of the cellular responses to double stranded RNA." *Virology* 219: 339-349.

Kaufman, H. and M. Disis (2004). "Immune system versus tumor: shifting the balance in favor of DCs and effective immunity." *J Clin Invest* 113(5): 664-667.

Levy, H. (1986). "Polynucleotides as interferon inducers and immune modulators." *J Bioact Compat Polym.* 1: 348-385.

Levy, H. and C. Bever (1988). Immune modulating effects of PICLC in mice, monkeys, and man. *Applied Bioactive Polymers*. C. Carraher and V. Foster. New York, Plenum.

Levy, H. and E. Lvovsky (1978). "Topical treatment of vaccinia virus infecton with an interferon inducer in rabbits." *J Infect Dis* 137(1): 78-81.

Marcus, P. and M. Sekellick (2001). "Combined sequential treatment with interferon and dsRNA abrogates virus resistance to interferon action." *J. Interferon Cytokine Res* 21: 423-429.

Mattei, F., G. Schiavoni, et al. (2001). "IL-15 is expressed by dendritic cells in response to type I IFN, dsRNA, or lipopolysaccharide and promotes dendritic cell activation." *Journal of Immunology* 167: 1179-1187.

Pantaleo, G. and R. Koup (2004). "Correlates of immune protection in HIV-1 infection: what we know, what we don't know, what we should know." *Nature Medicine* 10(8): 806-810.

Ponsaerts, P., G. Van den Bosch, et al. (2002). "Messenger RNA electroporation of human monocytes followed by rapid in vitro differentiation, leads to highly stimulatory antigen loaded mature dendritic cells." *Journal of Immunology* 169: 1669-1675.

Rosenberg, S., J. Yang, et al. (2004). "Cancer immunotherapy: moving beyond current vaccines." *Nat Med* 10(9): 909-15.

Salazar, A., H. Levy, et al. (1996). "Long-term IM Poly-ICLC treatment of malignant glioma: an open pilot study." *Neurosurgery* 38(6): 1096-1104.

Salazar, A., J. Morales, et al. (1990). "Intramuscular Poly-ICLC in HIV Infection: Preliminary findings." *Neurology* 40(Suppl 1): 238.

Salem, M., A. Kadima, et al. (2005). "Defining the antigen specific T-cell response to vaccination and Poly(I:C)/TLR3 signaling." *J Immunother* 28(3): 220-228.

Sen, G. and S. Sarkar (2005). "Transcriptional signaling by double stranded RNA: role of TLR3." *Cytokine & Growth Factor Reviews* 16: 1-14.

Shurin, G., M. Shurin, et al. (2001). "Neuroblastoma-derived gangliosides inhibit dendritic cell generation and function." *Cancer Research* 61: 363-369.

Spisek, R., G. Bougras, et al. (2003). "Transient exposure of dendritic cells to maturation stimuli is sufficient to induce complete phenotypic maturation while preserving their capacity to respond to subsequent restimulation." *Cancer Immunol Immunother* 52: 445-454.

Stephen, E., D. Hilmas, et al. (1977). "Swine influenza virus vaccine: potentiation of antibody responses in rhesus monkeys." *Science* 197: 1289-1290.

Su, Y., S. Sohn, et al. (2004). "Selective CD4+ Lymphopenia in melanoma patients treated with temozolomide: a toxicity with therapeutic implications." *J Clin Oncol* 22: 610-616.

Sutmuller, R., L. van Duivernvoorde, et al. (2001). "Synergis of cytotoxic T lymphocyte-associated antigen 4 blockeade and depletion of CD25 regulatory T cells in antitumor therapy reveals alternative pathways for suppression of autoreactive cytotoxic T lymphocyte responses." *J Exp Med* 194(6): 823-832.

Verjdijk, R., T. Mutis, et al. (1999). "Polyriboinosinic Polyribocytidylic Acid (Poly I:C) induces stable maturation of functionally active human dendritic cells." *Journal of Immunology* 163: 57-61.

Warfield, K., P. J G, et al. (2004). "Role of natural killer cells in innate protection against lethal ebola virus infection." *J Exp Med* 200(2): 169-79.

Wong, J., E. Saravolac, et al. (1995). "Prophylactic and therapeutic efficacies of poly(ICLC) against respiratory influenza A virus infection in mice." *Antimicrob Agents Chemother* 39(11): 2574-2576.

Yoneyama, M., M. Kikuchi, et al. (2004). "The RNA helicase RIG-1 has an essential function in dsRNA induced innate antiviral responses." *Nature Immunology* 5(7): 730-737.

The invention claimed is:

1. A method of immunotherapy of human disease caused by malignant brain tumors, melanoma, prostate, breast, ovarian, cervical, lung, liver, pancreatic, and colon cancer; and disease caused by chronic infection with Human Immunodeficiency virus, and Human Papilloma Virus; comprising the steps of: administering specific pathogen-associated antigen, either mixed with or given separately at the same time and in the same location in the patient's body with Poly-ICLC that has been formulated using poly-1-lysine of 13,000 to 28,000 molecular weight and poly IC of at least one million molecular weight, and is administered in at least one or more doses spaced 4-72 hours apart, at a dose of 1 to 50 micrograms Poly-ICLC per kg body weight in humans, wherein said antigen is comprised of a protein, a peptide, a dendritic cell platform, a DNA platform, a viral vector platform, cell extracts, polysaccharides, lipids, glycolipids, carbohydrates, killed virus, and viral extracts, and wherein cells stimulated by poly-ICLC are comprised of host dendritic cells, pre-dendritic cells, or myeloid dendritic cells, or plasmacytoid dendritic cells, macrophages, host T-cells, including CD4+, CD8+, Cytotoxic T-lymphocytes, T-reg cells, and host B-cells.

* * * * *